(12) United States Patent
Hamanaka et al.

(10) Patent No.: US 11,234,593 B2
(45) Date of Patent: Feb. 1, 2022

(54) SLIT LAMP MICROSCOPE

(71) Applicant: RIGHT MFG. CO., LTD., Tokyo (JP)

(72) Inventors: Norikazu Hamanaka, Tokyo (JP);
Hajime Hakamada, Tokyo (JP);
Kotaro Kawanishi, Tokyo (JP);
Keisuke Suzuki, Tokyo (JP)

(73) Assignee: RIGHT MFG. CO., LTD., Tokyo (JP)

( * ) Notice: Subject to any disclaimer, the term of this patent is extended or adjusted under 35 U.S.C. 154(b) by 231 days.

(21) Appl. No.: 16/604,424

(22) PCT Filed: Apr. 13, 2017

(86) PCT No.: PCT/JP2017/015199
§ 371 (c)(1),
(2) Date: Oct. 10, 2019

(87) PCT Pub. No.: WO2018/189873
PCT Pub. Date: Oct. 18, 2018

(65) Prior Publication Data
US 2021/0290054 A1    Sep. 23, 2021

(51) Int. Cl.
*A61B 3/135* (2006.01)
*A61B 3/00* (2006.01)
*A61B 3/16* (2006.01)

(52) U.S. Cl.
CPC ............ *A61B 3/135* (2013.01); *A61B 3/0008* (2013.01); *A61B 3/165* (2013.01)

(58) Field of Classification Search
CPC ....... G02B 3/135; G02B 3/0008; G02B 3/165
(Continued)

(56) References Cited

U.S. PATENT DOCUMENTS 2,235,319 A * 3/1941 Jobe ..................... A61B 3/0075
351/200
2,940,357 A * 6/1960 Oswoldolufg ....... A61B 3/0075
351/245
(Continued)

FOREIGN PATENT DOCUMENTS

CN          2889160 Y      4/2007
CN        101828900 A      9/2010
(Continued)

OTHER PUBLICATIONS

International Search Report and Written Opinion for PCT Patent App. No. PCT/JP2017/015199 (dated May 16, 2017) with English translation of the ISR.

*Primary Examiner* — Zachary W Wilkes
(74) *Attorney, Agent, or Firm* — Cermak Nakajima & McGowan LLP; Tomoko Nakajima

(57) ABSTRACT

In a slit lamp microscope, ease of maintenance of an illumination-power-supply cable is improved while preventing the cable from appearing untidy. An illumination support arm of a slit lamp microscope is provided with a groove-shaped cable holder in which the illumination-power-supply cable is disposed along the outer surface of the illumination support arm in an externally exposed state. This configuration facilitates replacement of the illumination-power-supply cable even when a problem, such as breaking of the illumination-power-supply cable, occurs, thus improving ease of maintenance. Furthermore, because the illumination-power-supply cable is disposed along the groove-shaped cable holder, the slit lamp microscope has a neat appearance.

11 Claims, 11 Drawing Sheets

(58) Field of Classification Search
USPC .......................................... 351/214; 362/258
See application file for complete search history.

(56) References Cited

U.S. PATENT DOCUMENTS

| | | | | | |
|---|---|---|---|---|---|
| 3,407,019 | A | * | 10/1968 | Wilkinson | A61B 3/107 351/214 |
| 3,467,466 | A | * | 9/1969 | Binstead | A61B 3/135 351/211 |
| 3,944,342 | A | * | 3/1976 | Martinez | A61B 3/135 351/206 |
| 4,175,839 | A | * | 11/1979 | Muller | A61B 3/0075 351/213 |
| 4,331,392 | A | * | 5/1982 | Sato | A61B 3/135 351/214 |
| 4,411,502 | A | * | 10/1983 | Lang | A61B 3/135 351/206 |
| 4,504,129 | A | * | 3/1985 | Van Iderstine | A61B 3/14 351/206 |
| 4,554,917 | A | * | 11/1985 | Tagnon | A61F 9/008 606/4 |
| 5,424,788 | A | * | 6/1995 | Satake | A61B 3/0033 351/206 |
| 6,208,460 | B1 | * | 3/2001 | Degenhardt | G02B 21/0012 359/385 |
| 6,474,815 | B1 | * | 11/2002 | Ulbers | A61B 3/135 351/214 |
| 6,644,810 | B1 | * | 11/2003 | Ulbers | A61B 3/135 351/212 |
| 7,052,135 | B2 | * | 5/2006 | Takeda | A61B 3/0033 351/200 |
| 7,118,218 | B2 | * | 10/2006 | Barker | A61B 3/0083 351/214 |
| 7,922,329 | B1 | * | 4/2011 | Graether | A61B 3/135 351/205 |
| 9,687,149 | B2 | * | 6/2017 | Nara | A61B 3/156 |
| 2003/0184711 | A1 | | 10/2003 | Abe et al. | |
| 2003/0184712 | A1 | * | 10/2003 | Takeda | A61B 3/0033 351/245 |
| 2011/0187996 | A1 | | 8/2011 | Ueno et al. | |
| 2013/0286347 | A1 | * | 10/2013 | Teijido | A61B 3/132 351/206 |
| 2016/0095516 | A1 | | 4/2016 | Nara | |
| 2019/0365569 | A1 | * | 12/2019 | Skovgaard | A61N 5/0625 |

FOREIGN PATENT DOCUMENTS

| | | | |
|---|---|---|---|
| CN | 102138776 | A | 8/2011 |
| CN | 202960459 | U | 6/2013 |
| CN | 204555214 | U | 8/2015 |
| EP | 2695571 | A1 | 2/2014 |
| JP | 2002-102173 | A | 4/2002 |
| JP | 2002102173 | A * | 4/2002 |
| JP | 2003-275177 | A | 9/2003 |
| JP | 2003-290143 | A | 10/2003 |
| JP | 2003-299619 | A | 10/2003 |
| JP | 2004-290461 | A | 10/2004 |
| JP | 2004290461 | A * | 10/2004 |
| JP | 2014-033812 | A | 2/2014 |
| JP | 2016-067818 | A | 5/2016 |

* cited by examiner

SLIT LAMP MICROSCOPE

This application is a national phase entry under 35 U.S.C. § 371 of PCT Patent Application No. PCT/JP2017/015199, filed on Apr. 13, 2017, which is incorporated by reference.

TECHNICAL FIELD

The present invention relates to a slit lamp microscope, which is used to observe the eye to be examined while radiating slit light onto the eye.

BACKGROUND ART

Slit lamp microscopes are widely used to observe the condition of the eye to be examined in the ophthalmic field. The slit lamp microscopes in the related art include an illumination unit for radiating slit light onto the eye to be examined, and a microscope unit for observing the eye to be examined. The illumination unit and the microscope unit have an illumination support arm and a microscope support arm, respectively, and the illumination support arm and the microscope support arm are connected to each other by a common swivel shaft so as to be independently pivotable in the horizontal direction. By aligning the focal plane of the slit light radiated from the illumination unit onto the swivel shaft and the focal plane of the microscope, it is possible to illuminate and observe the eye to be examined at a desired angle.

A light source that radiates slit light is accommodated in the illumination unit. The slit light is radiated downward through an illumination optical system accommodated in the illumination unit, is reflected by a reflection mirror attached to the illumination support arm, and is radiated onto the eye to be examined. In a known system, power is supplied to the light source accommodated in the illumination unit through an illumination-power-supply cable suspended in the air between the upper part of a chin rest unit, to which an examinee is fixed, and the illumination unit (Patent Literature 1). In another known system, the illumination-power-supply cable is allowed to pass through the inner space of a hollow tubular illumination support arm without being exposed to the outside of the apparatus and is connected to the light source of the illumination unit (Patent Literature 2). In Patent Literature 2, not only the illumination-power-supply cable, but also a background-illumination-power-supply cable, which is connected to a background-illumination light source used when observation is performed with a microscope unit, is allowed to pass through the interior of the illumination support arm.

CITATION LIST

Patent Literature

PTL 1: Japanese Unexamined Patent Application Publication No. 2014-33812, FIG. 1
PTL 2: Japanese Unexamined Patent Application Publication No. 2016-67818, FIG. 3

SUMMARY OF INVENTION

Technical Problem

As described above, in the known slit lamp microscopes in the related art, there are various ways of disposing the illumination-power-supply cable. However, in a slit lamp microscope in which the illumination-power-supply cable is suspended in the air between the upper part of the chin rest unit and the illumination unit, as in Patent Literature 1, the cable can potentially serve as an obstacle during observation and appears untidy. Although Patent Literature 2 can solve this problem with Patent Literature 1, there is another problem in that, if the illumination-power-supply cable is allowed to pass through the interior of the illumination support arm, when, for example, a problem occurs in radiating the slit light, it is not possible to check the exterior condition of the illumination-power-supply cable or to replace the cable without removing the cable from the interior of the illumination support arm. This problem also occurs in a periodic check performed when there is no problem. Because the examination using the slit lamp microscope is essential in ophthalmologic diagnosis and treatment, it is desirable to minimize the period for which the slit lamp microscope cannot be used.

The present invention has been made in view of the above-described related art. An object of the present invention is, in a slit lamp microscope, to improve ease of maintenance of an illumination-power-supply cable while preventing the cable from appearing untidy.

Solution to Problem

To achieve the above-described object, the present invention is configured to have the following characteristics.

The present invention provides a slit lamp microscope including: an illumination unit that illuminates an eye to be examined; an illumination support arm to which the illumination unit is attached; a support base to which the illumination support arm is attached; and an illumination-power-supply cable disposed along the illumination support arm from the support base side to the illumination unit. The illumination support arm has a groove-shaped cable holder in which the illumination-power-supply cable is disposed along the outer surface of the illumination support arm in an externally exposed state.

According to the present invention, because the illumination support arm has a groove-shaped cable holder in which the illumination-power-supply cable is disposed along the outer surface of the illumination support arm in an externally exposed state, even when a problem, such as breaking of the illumination-power-supply cable, occurs, it is possible to easily replace the illumination-power-supply cable, thus improving the ease of maintenance. Furthermore, because the illumination-power-supply cable is disposed along the exterior, more specifically, in the groove-shaped cable holder, of the slit lamp microscope, there is no need to suspend the illumination-power-supply cable in the air, as in the related-art slit lamp microscope. Thus, it is possible to achieve a slit lamp microscope with a neat appearance.

The present invention may be configured such that the cable holder has a locking part that prevents the illumination-power-supply cable disposed therein from coming off.

According to the present invention, because the cable holder has a locking part, it is possible to reliably hold the illumination-power-supply cable.

The present invention may be configured such that: the illumination support arm has an arm body attached to the support base, and at least one columnar shaft extending from the arm body to the illumination unit; and the cable holder has a first groove-shaped holder provided in the arm body and a second groove-shaped holder provided in the shaft.

According to the present invention, the illumination support arm may be configured to have an arm body attached to the support base, and at least one columnar shaft extending from the arm body to the illumination unit. Also when the illumination support arm has a configuration like this, the cable holder may be configured as the first groove-shaped holder provided in the arm body and the second groove-shaped holder provided in the shaft. Hence, it is possible to hold the illumination-power-supply cable along the illumination support arm in an exposed state.

The present invention may be configured such that the first groove-shaped holder has a step portion that is formed in the outer surface of the arm body and constitutes a groove bottom surface and a groove side surface of the first groove-shaped holder, and a holding plate that constitutes a groove side surface facing the groove side surface of the step portion.

According to the present invention, because the first groove-shaped holder has a step portion that is formed in the outer surface of the arm body and constitutes a groove bottom surface and a groove side surface of the first groove-shaped holder, and a holding plate that constitutes a groove side surface facing the groove side surface of the step portion, even if the arm body does not have a linear shape but has a shape having a bent portion, it is possible to form the first groove-shaped holder by making the holding plate extend along the step portion of the arm body. With this first groove-shaped holder, it is possible to hold the illumination-power-supply cable along the arm body in an exposed state.

The present invention may be configured such that: the second groove-shaped holder has a holding groove extending in the longitudinal direction of the shaft, and the holding groove has a guide slope that gently bends and guides the illumination-power-supply cable.

According to the present invention, because the second groove-shaped holder has a holding groove extending in the longitudinal direction of the shaft, it is possible to hold the illumination-power-supply cable along the shaft in an exposed state. Because the holding groove has a guide slope that gently bends and guides the illumination-power-supply cable, it is possible to gently guide the illumination-power-supply cable without sharply bending the illumination-power-supply cable toward the holding groove. Thus, it is possible to protect the illumination-power-supply cable.

The present invention may be configured such that a deformation allowance groove that allows flexural deformation of the illumination-power-supply cable is provided between the arm body and the shaft.

According to the present invention, because a deformation allowance groove is provided between the arm body and the shaft, the illumination-power-supply cable can be smoothly deformed in that position. This structure is especially effective when the central axis of the arm body and the central axis of the shaft are shifted from each other in a crank shape, because the illumination-power-supply cable needs to be disposed so as to be bent in a crank shape from the arm body to the shaft. Furthermore, it is also effective when the shaft is movable relative to the arm body. That is, when the shaft moves relative to the arm body, a portion of the illumination-power-supply cable fixed to the shaft moves relative to a portion of the illumination-power-supply cable fixed to the non-moving arm body. In this case, in the present invention, because the illumination-power-supply cable can be smoothly deformed in the deformation allowance groove, the shaft can also be smoothly moved.

The present invention may be configured to further include a microscope unit that is used to observe the eye to be examined, and a microscope support arm that is attached to the microscope unit at the distal end thereof and is attached to the support base at the base end thereof, wherein the microscope support arm has a background-illumination light source that illuminates the eye to be examined.

When the illumination unit radiates slit light onto the eye to be examined, the portion irradiated with only the slit light looks clear, but the other peripheral portion looks dark, which makes it difficult to identify the position of the disease. Hence, the background illumination is used to irradiate the eye to be examined from an optical path different from the optical path of the slit light. There are various types of background illumination, and, for example, in a known type, a light source is provided in the illumination unit (for example, see Patent Literature 2). However, if the light source for background illumination is disposed in the illumination unit, the radiation angle of the background illumination with respect to the eye to be examined is affected, depending on the position of the illumination unit.

In contrast, in the present invention, because the microscope support arm for supporting the microscope unit has the background-illumination light source for illuminating the eye to be examined, it is possible to uniformly radiate the background illumination light from the front side, from which the eye to be examined is observed with the microscope unit. Hence, it is possible to perform accurate observation.

The present invention may be configured such that the background-illumination light source is disposed at a position opposite the illumination support arm.

When the light intensity of the background illumination is to be adjusted, a mechanism for physically reducing the light intensity or a circuit for electrically adjusting the light is provided. In some observation methods, such as the retro illumination, the background illumination is not required. In such a case, the observer needs to turn on or off the background illumination each time, which is troublesome.

In contrast, in the present invention, because the background-illumination light source is located opposite the illumination support arm, when the background illumination is not required as in the retro illumination, it is possible to block the light radiated by the background-illumination light source with the illumination support arm. Hence, it is possible to omit a troublesome operation, in which the observer turns on or off the background-illumination light source each time, thus enabling stress-free and smooth observation.

The present invention may be configured to further include a background-illumination-power-supply cable, wherein the microscope support arm has a hollow tubular inner space, and the background-illumination-power-supply cable is disposed through the inner space of the microscope support arm, from the support base side to the background-illumination light source.

According to the present invention, because the illumination-power-supply cable and the background-illumination-power-supply cable can be disposed separately, maintenance thereof is easy. Furthermore, because the background-illumination-power-supply cable is disposed in the inner space of the microscope support arm and is not exposed to the outside, it is possible to achieve a slit lamp microscope with a neat appearance.

The present invention may be configured to further include a swivel shaft that allows the illumination support arm to pivot in the horizontal direction, relative to the support base, wherein the swivel shaft may have a pivot restricting portion that restricts a pivot area of the illumination support arm.

The slit lamp microscope is configured such that the illumination unit and the microscope unit can each be pivoted by 90 degrees or more to the left and right sides in the horizontal direction, with the eye to be examined being located in on the front side. In an disease in which the shape of the cornea has changed, such as that of a patient with keratoconus, sometimes the microscope unit is pivoted to the side surface of the slit lamp microscope when performing observation. However, in this case, depending on the position of the illumination unit, the center of gravity of the entire portion located above the support base moves toward the examinee, and the slit lamp microscope may be inclined toward the examinee.

In contrast, in the present invention, while the swivel shaft allows the illumination support arm to pivot in the horizontal direction, the pivot restricting portion restricts the pivot area of the illumination support arm. Hence, it is possible to reduce the risk that the illumination support unit comes into contact with the examinee as a result of pivoting.

The present invention may be configured to further include a standing-type tonometer above the swivel shaft of the support base.

In the slit lamp microscope of the present invention, the illumination-power-supply cable is not allowed to pass through the inner space of the illumination support arm, but is disposed along the outer surface of the illumination support arm. Hence, it is possible to ensure a sufficient space between the upper part of the swivel shaft and the illumination support arm, thus making it possible to provide the standing-type tonometer.

Advantageous Effects of Invention

With the slit lamp microscope of the present invention, it is possible to improve ease of maintenance of the illumination-power-supply cable, while disposing the illumination-power-supply cable neatly.

BRIEF DESCRIPTION OF DRAWINGS

FIG. 4 includes views showing a shaft in FIG. 1, in which

FIG. 8 includes views of a swivel shaft provided in the slit lamp microscope in FIG. 1, in which

DESCRIPTION OF EMBODIMENTS

Figure 1:
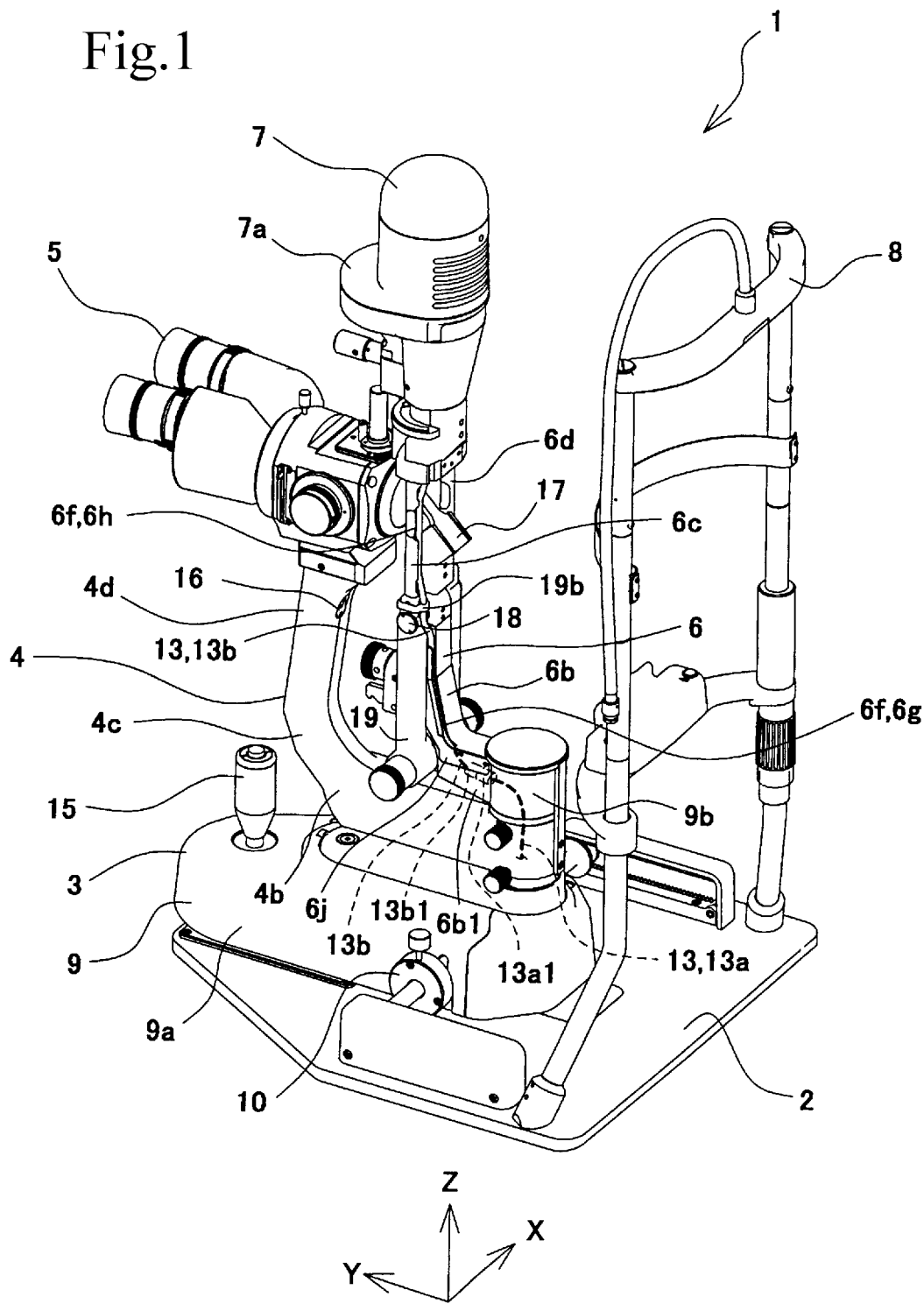
FIG. 1 is a perspective view including views of a right side surface, a back surface, and a top surface of a slit lamp microscope according to an embodiment.

An embodiment of a slit lamp microscope of the present invention will be described with reference to the drawings. In the Description and Claims, for ease of explanation, the left-right direction and the width direction as viewed from the front side of the slit lamp microscope will be referred to as the X direction, the front-rear direction and the depth direction will be referred to as the Y direction, and the top-bottom direction and the height direction will be referred to as the Z direction.

[Overall Structure of Slit Lamp Microscope]

A slit lamp microscope 1 includes a mounting frame 2, a sliding base 3, a microscope support arm 4, a microscope unit 5, an illumination support arm 6, an illumination unit 7, and a chin rest unit 8.

The mounting frame 2 is formed in a flat plate shape, and the sliding base 3 and the chin rest unit 8 are provided on the top surface of the mounting frame 2.

The sliding base 3 constitutes a "support base" of the present invention and includes a base body 9, a driving unit 10, and a swivel shaft 11.

The base body 9 accommodates, in the interior thereof, a substrate 12 having a light-adjusting circuit, and an illumination-power-supply cable 13 and a background-illumination-power-supply cable 14 are connected to the substrate 12.

Figure 2:
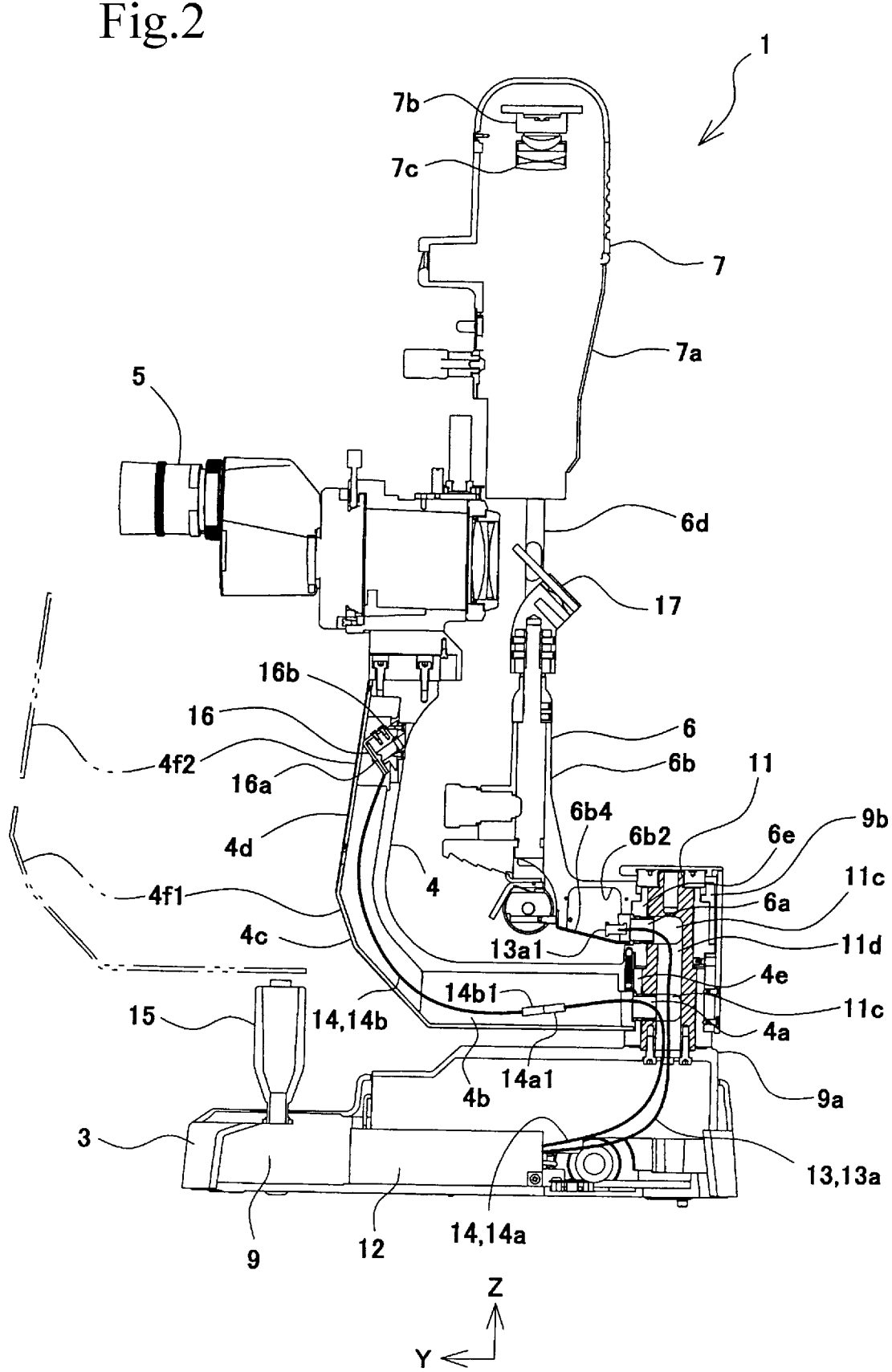
FIG. 2 is a schematic vertical sectional view of the slit lamp microscope in FIG. 1, taken along the central axis in front view.
Figure 3:
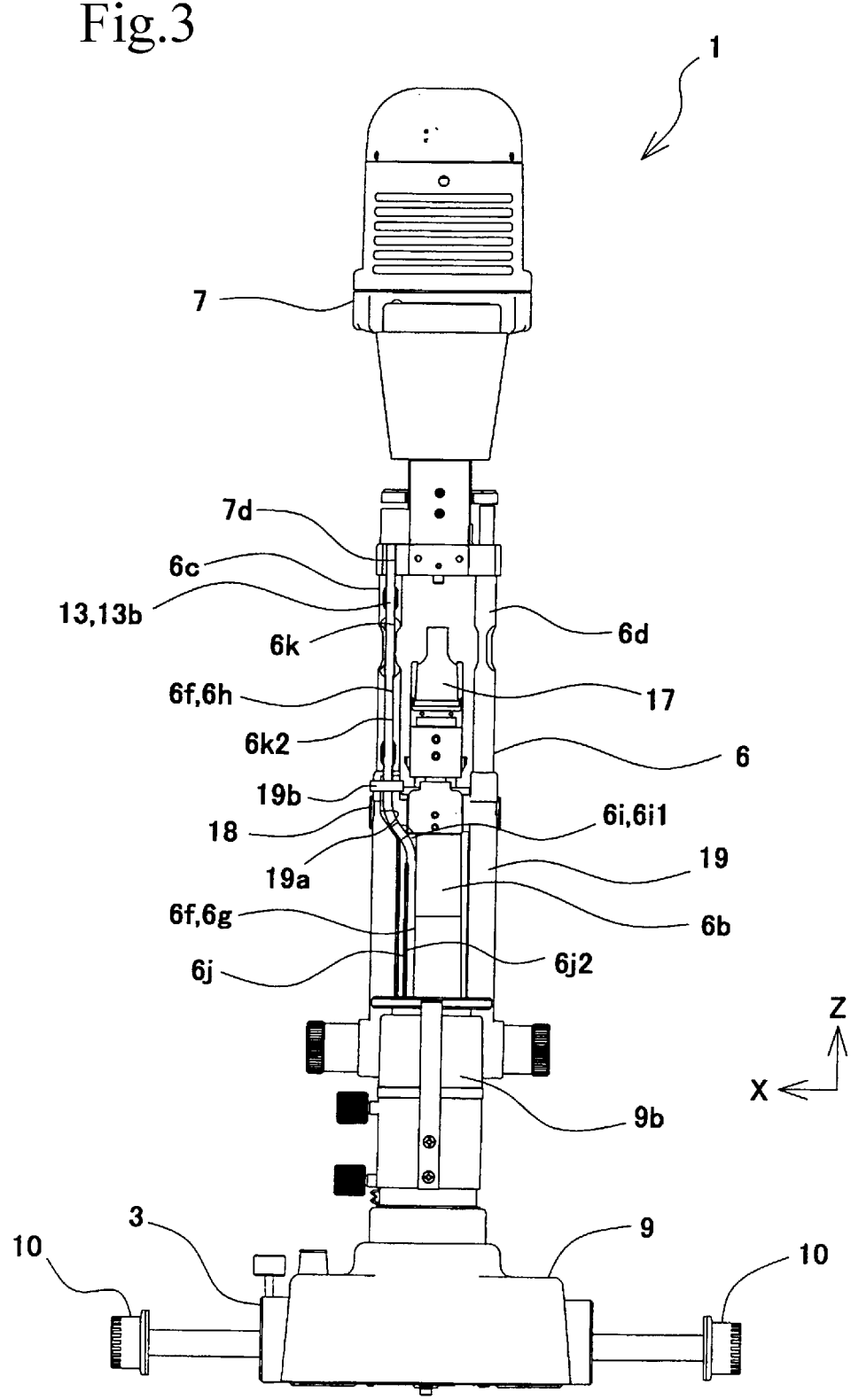
FIG. 3 is a back view of an illumination unit, an illumination support arm, and a sliding base in FIG. 1.
Figures 4A, 4B:
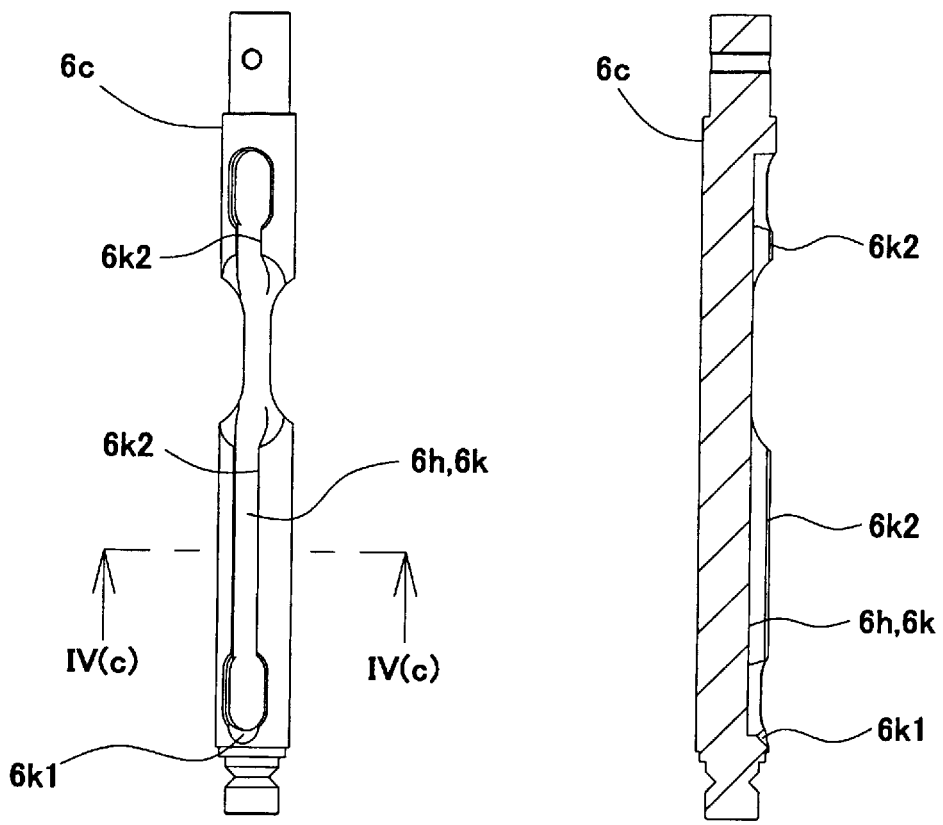
FIG. 4(a) is a back view.
FIG. 4(b) is a vertical sectional view taken along the central axis in front view.
Figure 4C:
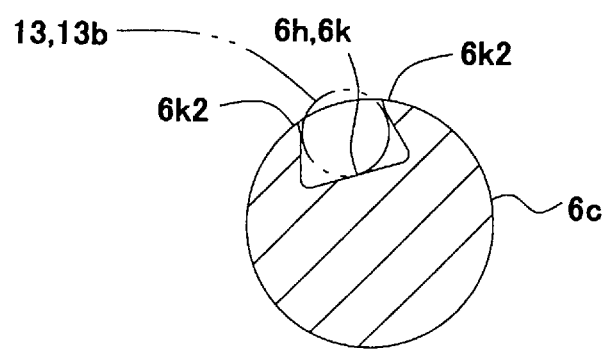
FIG. 4(c) is an enlarged sectional view taken along line IV-IV in FIG. 4(a).
Figure 5:
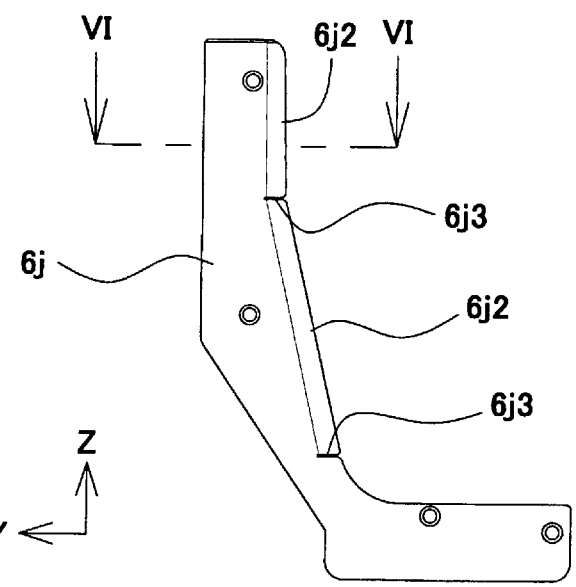
FIG. 5 is a right side view of a holding plate in FIG. 1.
Figure 6:
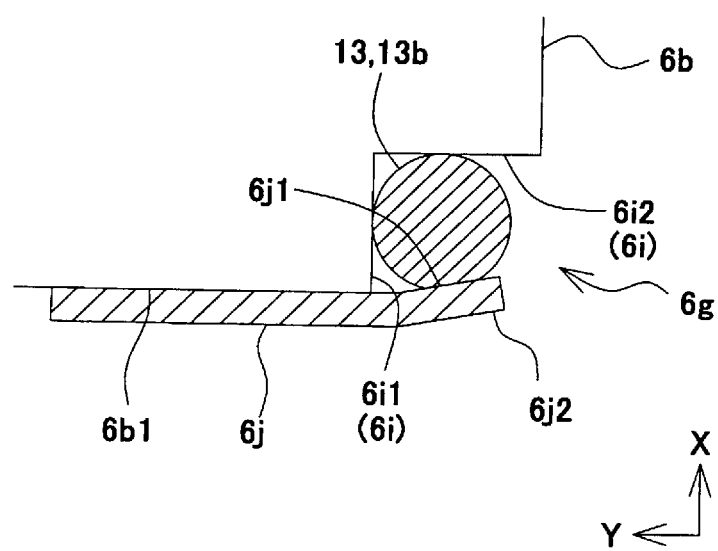
FIG. 6 is a sectional view of a second groove-shaped holder, taken along line VI-VI in FIG. 5.
Figure 7:
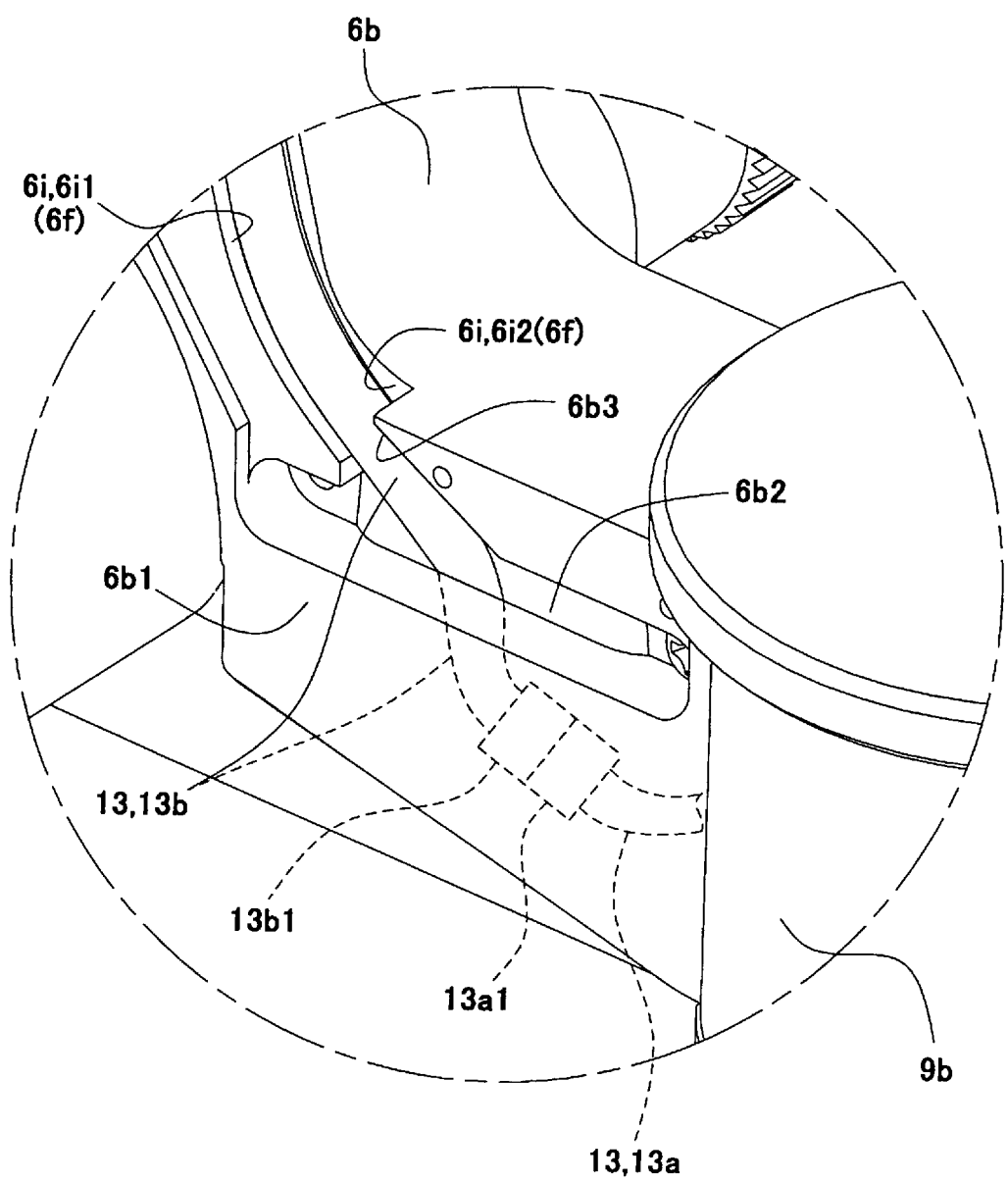
FIG. 7 is a partial enlarged perspective view of the slit lamp microscope in FIG. 1, showing an illumination-power-supply cable disposed from a connecting hollow part to a cable holder, in a state in which the holding plate is removed.

The illumination-power-supply cable 13 includes a substrate-side cable 13a and an illumination-unit-side cable 13b. By conductively connecting a connector 13a1 provided on the substrate-side cable 13a and a connector 13b1 provided on the illumination-unit-side cable 13b, power is supplied from the substrate 12 to the illumination unit 7. As shown in FIG. 2, the connector 13a1 on the substrate-side cable 13a is disposed in a connecting hollow part 6b2, in which a cable protection tube 6a located at the base end of the illumination support arm 6 (described below) projects, and is conductively connected to the connector 13b1 of the illumination-unit-side cable 13b. As shown in FIG. 7, the illumination-unit-side cable 13b is guided into a cable holder 6f through a communication port 6b3 located at the boundary between the connecting hollow part 6b2 and the cable holder 6f. The connecting hollow part 6b2 can be opened and closed by a cover 6b4, which can be attached to and removed from the bottom surface of the illumination support arm 6, to facilitate tasks required in wiring or maintenance.

Similarly to the illumination-power-supply cable 13, the background-illumination-power-supply cable 14 also includes a substrate-side cable 14a and a background-illumination-unit-side cable 14b, and, by conductively connecting a connector 14a1 provided on the substrate-side cable 14a and a connector 14b1 provided on the illumination-unit-side cable 14b, power is supplied from the substrate 12 to the background-illumination unit 16.

The driving unit 10 includes a driving mechanism that moves the base body 9 in the X and Y directions by operating a joystick 15.

The swivel shaft 11 is formed in a cylindrical shape. A lower attachment part 11a for the microscope support arm 4 and an upper attachment part 11b for the illumination support arm 6 are formed on the outer circumferential surface of the swivel shaft 11. The swivel shaft 11 is fixed to a tubular accommodating part 9b of the housing 9a of the base body 9 with bolts. The lower attachment part 11a and the upper attachment part 11b are provided with movement-allowing holes 11c, which communicate with a cable insertion hole 11d extending in the axial direction of the swivel shaft 11. The substrate-side cable 13a of the illumination-power-supply cable 13, which is connected to the substrate 12, is inserted into the cable insertion hole 11d from the lower-end opening of the swivel shaft 11 and enters into the interior of the illumination support arm 6 from the cable protection tube 6a, which is inserted into the movement-allowing hole 11c in the upper attachment part 11b and projects from the base end of the illumination support arm 6. On the other hand, the substrate-side cable 14a of the background-illumination-power-supply cable 14 is also inserted into the cable insertion hole 11d from the lower-end opening of the swivel shaft 11 and is inserted into the interior of the microscope support arm 4 from the cable protection tube 4a, which is inserted into the movement-allowing hole 11c in the lower attachment part 11a and projects from the base end of the microscope support arm 4.

The microscope support arm 4 is formed in the shape of a hollow square pipe and includes a first extending part 4b extending forward from the swivel shaft 11 in the Y direction, a bent portion 4c bent upward in the Z direction from the end of the first extending part 4b, and a second extending part 4d extending upward in the Z direction from the bent portion 4c. A fitting part 4e, which is pivotably attached to the outer circumference of the lower attachment part 11a of the swivel shaft 11, is provided at the base end of the first extending part 4b, and the cable protection tube 4a to be inserted into the movement-allowing hole 11c projects at the fitting part 4e. The connector 14a1 of the substrate-side cable 14a of the background-illumination-power-supply cable 14 and the connector 14b1 of the background-illumination-unit-side cable 14b are conductively connected to each other inside the first extending part 4b. As shown in FIG. 2, two covers 4f1 and 4f2 are removably attached to the microscope support arm 4. Inspection and replacement of the background-illumination unit 16 (described below) and the background-illumination-power-supply cable 14 can be easily performed by removing the covers 4f1 and 4f2 from the microscope support arm 4. The microscope unit 5, which is used to observe the eye to be examined, is attached at the upper end of the second extending part 4d.

Furthermore, the background-illumination unit 16 is attached to the second extending part 4d, below the microscope unit 5. The background-illumination unit 16 is attached so as not to project from the outer surface of the second extending part 4d, thereby improving the design quality such that the microscope support arm 4 has a neat appearance. The background-illumination unit 16 includes a background-illumination light source 16a and an optical system 16b. The background-illumination-power-supply cable (background-illumination-unit-side cable 14b) extending from the substrate 12 through the swivel shaft 11 and the microscope support arm 4 is connected to the background-illumination light source 16a.

The illumination support arm 6 includes an arm body 6b, which projects forward in the Y direction from the swivel shaft 11 and is bent so as to extend upward, and two shafts 6c and 6d extending upward in the Z direction from the arm body 6b.

The arm body 6b is provided with, at the base end thereof, a fitting part 6e pivotably attached to the outer circumference of the upper attachment part 11b of the swivel shaft 11, and the cable protection tube 6a inserted into the movement-allowing hole 11c projects from the fitting part 6e. A reflection mirror 17 is attached at the upper end of the arm body 6b. A pivot shaft 18 extending in the X direction is provided at the base end of the reflection mirror 17 and the shafts 6c and 6d. The pivot shaft 18 allows the illumination unit 7, including the shafts 6c and 6d, and the support frame 19, which extends parallel to the arm body 6b and supports the lower ends of the shafts 6c and 6d, to pivot about the X axis, relative to the arm body 6b, so as to face up. The upper ends of the two shafts 6c and 6d are fixed to the lower end portion of a housing 7a of the illumination unit 7.

The illumination support arm 6 has, in the outer surface thereof, the groove-shaped cable holder 6f for holding the illumination-unit-side cable 13b of the illumination-power-supply cable 13. The cable holder 6f includes a first groove-shaped holder 6g, which is provided in the outer surface of the arm body 6b, and a second groove-shaped holder 6h, which is provided in the outer surface of the shaft 6c.

The first groove-shaped holder 6g is formed of a step portion 6i formed in the outer surface of the arm body 6b, and a holding plate 6j attached along the step portion 6i. The step portion 6i includes a groove bottom surface 6i1 and a groove side surface 6i2. The holding plate 6j is formed as a groove side surface 6j1 facing the groove side surface 6i2 of the step portion 6i. The step portion 6i is formed such that a corner of the arm body 6b is recessed inward in a step shape, from the base end to the upper end of the arm body 6b. The holding plate 6j is formed in a shape conforming to the bent shape of the arm body 6b and covering the side of the step portion 6i. The holding plate 6j is provided with a holding part 6j2, serving as a "locking part", for preventing the illumination-unit-side cable 13b from coming off. The holding plate 6j is made of a thin metal plate, and the holding part 6j2 is formed by bending the upper edge of the holding plate 6j toward the step portion 6i. To make bending easy, the holding plate 6j is provided with a slit 6j3. The holding plate 6j is removably screwed to the side surface 6b1 of the arm body 6b.

The second groove-shaped holder 6h is formed as a holding groove 6k extending in the longitudinal direction of the shaft 6c. The holding groove 6k has, at the lower end thereof, a guide slope 6k1 that gently bends and guides the illumination-unit-side cable 13b of the illumination-power-supply cable 13 to the holding groove 6k. Because it is possible to gently guide the illumination-unit-side cable 13b into the holding groove 6k without sharply bending the cable 13b, it is possible to protect the illumination-unit-side cable 13b. Furthermore, because the provision of the holding groove 6k reduces the amount of the illumination-unit-side cable 13b projecting from the outer circumferential surface of the shaft 6c, loss of field of view due to the illumination-unit-side cable 13b, which occurs when observation is performed using the microscope unit 5, hardly occurs. In other words, the holding groove 6k is formed to have a depth that does not cause the loss of field of view. Furthermore, the holding groove 6k is provided with holding parts 6k2, projecting toward the opening of the holding groove 6k and serving as "locking parts" for preventing the illumination-unit-side cable 13b held therein from coming off.

The central axis of the first groove-shaped holder 6g and the central axis of the second groove-shaped holder 6h are shifted from each other in the X direction. Hence, the illumination-unit-side cable 13b needs to be disposed so as to be bent in a crank shape in accordance with the shifting of the central axes. For this purpose, the support frame 19, which extends parallel to the arm body 6b in the Z direction and supports the lower end of the shaft 6c, is provided with a deformation allowance groove 19a for the illumination-power-supply cable 13. The support frame 19 and the shaft 6c are allowed to pivot by the pivot shaft 18. When the support frame 19 and the shaft 6c move relative to the arm body 6b, a portion of the illumination-unit-side cable 13b fixed to the shaft 6c moves relative to a portion of the illumination-unit-side cable 13b fixed to the arm body 6b, which does not move. In this case, because the illumination-unit-side cable 13b can be smoothly deformed in the deformation allowance groove 19a, the support frame 19 and the shaft 6c can also be smoothly pivoted. A cable holder 19b, which holds the deformed illumination-unit-side cable 13b such that the central axis thereof is aligned with the central axis of the second groove-shaped holder 6h, is provided above the deformation allowance groove 19a. The cable holder 19b is provided with an insertion hole, and the illumination-unit-side cable 13b is inserted and held therein.

Figure 9:
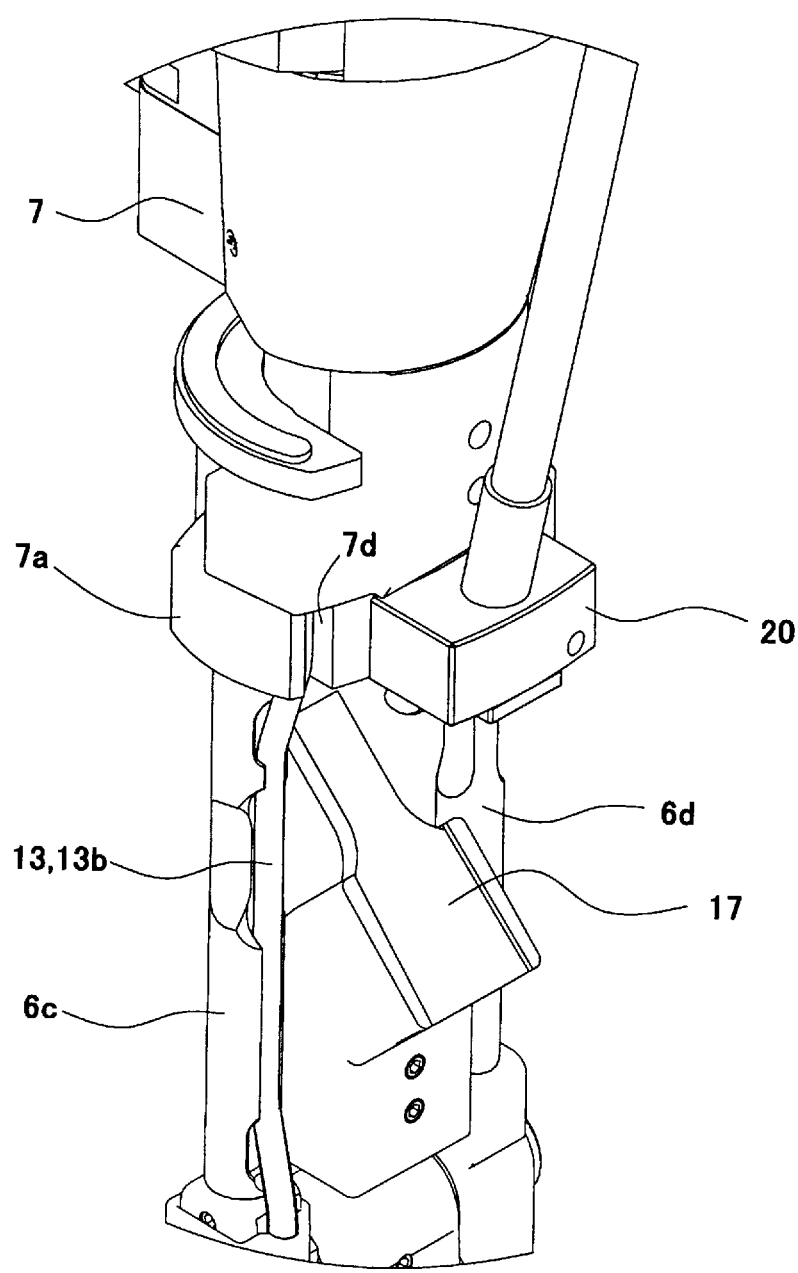
FIG. 9 is an enlarged perspective view of a relevant part including views of the right side surface, the back surface, and the top surface, showing a state in which a light-source-diverting-type background illumination device is attached to the slit lamp microscope in FIG. 1.

In the illumination unit 7, a light source 7b is disposed inside the housing 7a. The light emitted from the light source 7b is radiated downward via an illumination optical system 7c, is reflected by the reflection mirror 17 provided at an intermediate position, and is radiated, in the form of slit light, onto the eye to be examined. The housing 7a of the illumination unit 7 has, in the lower end, a cable insertion groove 7d, from which the illumination-unit-side cable 13b is guided into the housing 7a and is connected to the light source 7b. The cable insertion groove 7d accommodates the illumination-unit-side cable 13b inserted therein such that the cable 13b does not project outside. Hence, an attachment can be attached to a nearby portion. An example attachment is, as shown in, for example, FIG. 9, a light-source-diverting-type background illumination device 20, which uses the light from the light source 7b for background illumination by using an optical fiber.

[Effects and Advantages of Slit Lamp Microscope 1]

Next, effects and advantages of the thus-configured slit lamp microscope 1 will be described, except for those that have already been described above.

[Ease of Maintenance]

The slit lamp microscope 1 has a groove-shaped cable holder 6f, in which the illumination-unit-side cable 13b of the illumination-power-supply cable 13 is disposed along the outer surface of the illumination support arm 6 in an externally exposed state, and the illumination-unit-side cable 13b is disposed in a state of being exposed on the outer surface of the illumination support arm 6. Hence, even when a problem, such as breaking of the illumination-unit-side cable 13b, occurs, the illumination-unit-side cable 13b can be easily replaced, improving the ease of maintenance. In such a situation, because it is possible to replace the illumination-unit-side cable 13b by removing a protection cover 6j and detaching the connector 13b1 of the illumination-unit-side cable 13b from the connector 13a1 on the substrate-side cable 13a, there is no need to replace the overall illumination-power-supply cable 13. On the other hand, when the substrate-side cable 13a has a problem, it is possible to remove only the substrate-side cable 13a for replacement. Furthermore, because there is no need to suspend the illumination-power-supply cable 13 in the air, as in the related-art slit lamp microscope in Patent Literature 1, it is possible to achieve a slit lamp microscope 1 with a neat appearance. Unlike the related-art slit lamp microscope in Patent Literature 2, in which the illumination-power-supply cable is allowed to pass through the inner space of the hollow tubular illumination support arm so as not to be exposed outside, the illumination-unit-side cable 13b appears on the exterior of the slit lamp microscope 1. However, by arranging the illumination-unit-side cable 13b along the cable holder 6f as described above, it is possible to dispose the cable in a neat manner while ensuring ease of maintenance.

[Ease of Wiring Task]

When the illumination-unit-side cable 13b is disposed in the first groove-shaped holder 6g, for example, the holding plate 6j is slightly bent outward to widen the opening, and then the illumination-unit-side cable 13b is pushed therein. Alternatively, after the illumination-unit-side cable 13b is positioned in the step portion 6i, the holding plate 6j is screwed to the side surface 6b1 of the arm body 6b. This way, the illumination-unit-side cable 13b can be easily disposed in the first groove-shaped holder 6g. Furthermore, also when the illumination-unit-side cable 13b is disposed in the holding groove 6k, serving as the second groove-shaped holder 6h, the illumination-unit-side cable 13b can be easily disposed in the holding groove 6k by pushing the illumination-unit-side cable 13b into the holding groove 6k while gently bending the illumination-unit-side cable 13b along the guide slope 6k1.

[Rotation Restriction of Microscope Support Arm 4 and Illumination Support Arm 6]

Figures 8A, 8B:
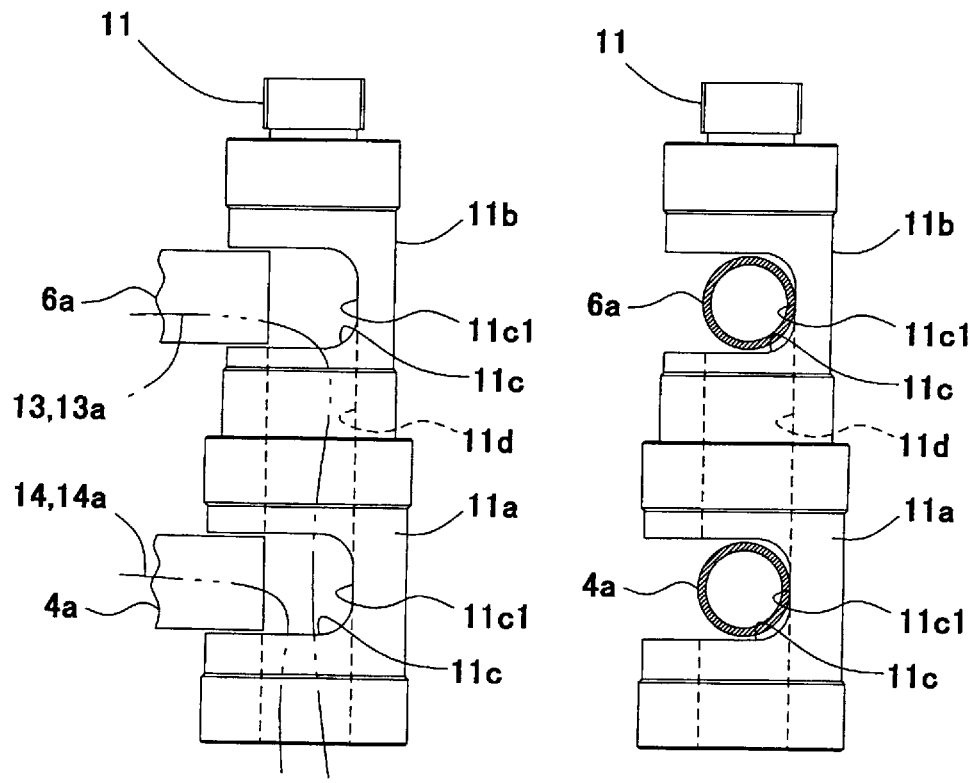
FIG. 8(a) is a right side view.
FIG. 8(b) is a right side view showing a state in which the illumination support arm and the microscope support arm have been pivoted by 90 degrees.
Figure 8C:
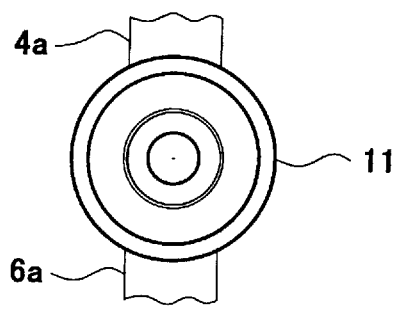
FIG. 8(c) is a plan view showing a state in which the illumination support arm and the microscope support arm have been pivoted in opposite directions by 90 degrees from the front side.

The cable protection tube 4a of the microscope support arm 4 and the cable protection tube 6a of the illumination support arm 6 are inserted into the corresponding movement-allowing holes 11c in the swivel shaft 11. The microscope support arm 4 and the illumination support arm 6 are rotatable relative to the swivel shaft 11, and, in accordance with the rotation thereof, the cable protection tubes 4a and 6a also pivot in the movement-allowing holes 11c. As shown in FIGS. 8(b) and 8(c), when the cable protection tubes 4a and 6a are located at the positions rotated by 90 degrees in the right and left directions from the front side, the cable protection tubes 4a and 6a come into contact with hole edges 11c1, serving as "pivot restricting portions", at the right and left ends of the movement-allowing holes 11c, and further rotation of the microscope support arm 4 and the illumination support arm 6 is restricted. Hence, the center of gravity of the entire portion located above the sliding base 3 does not move toward the chin rest unit 8, that is, toward the examinee due to the weight and momentum of the rotated microscope unit 5 and illumination unit 7, thus making it possible to safely conduct an examination.

[Background-Illumination Unit 16]

The microscope support arm 4 according to the embodiment is provided with the background-illumination unit 16 for illuminating the eye to be examined. Because this makes it possible to uniformly radiate the background-illumination light from the front side, from which the eye to be examined is observed with the microscope unit 5, it is possible to perform accurate observation.

The background-illumination unit 16 is located at a position opposite the arm body 6b of the illumination support arm 6. As in the retro illumination, the background illumination is not required depending on the observation method. In such a case, the observer needs to turn on or off the background illumination each time. However, when the background illumination is not required, it is possible to block the light radiated by the background-illumination light source 16a with the illumination support arm 6. Hence, it is possible to omit a troublesome operation, in which the observer turns on or off the background-illumination light source 16a each time, thus enabling stress-free and smooth observation.

Because the microscope support arm 4 has a hollow tube shape to allow the background-illumination-power-supply cable 14 to pass therethrough, the illumination-power-supply cable 13 and the background-illumination-power-supply cable 14 can be disposed separately, and thus, maintenance thereof is easy. Furthermore, because the background-illumination-power-supply cable 14 is disposed in the inner space of the microscope support arm 4 and is not exposed to the outside, it is possible to achieve a slit lamp microscope 1 with a neat appearance. Maintenance and replacement of the background-illumination unit 16 and the background-illumination-power-supply cable 14 can be easily performed by removing the covers 4f1 and 4f2 of the microscope support arm 4, as shown in FIG. 2. Furthermore, because the background-illumination-power-supply cable 14 is divided into the substrate-side cable 14a and the background-illumination-unit-side cable 14b, which are removably attached to each other by connectors 14a1 and 14b1, it is also easy to replace only one of the substrate-side cable 14a and the background-illumination-unit-side cable 14b.

[Creating Installation Space for Standing-Type Tonometer]

Figure 10:
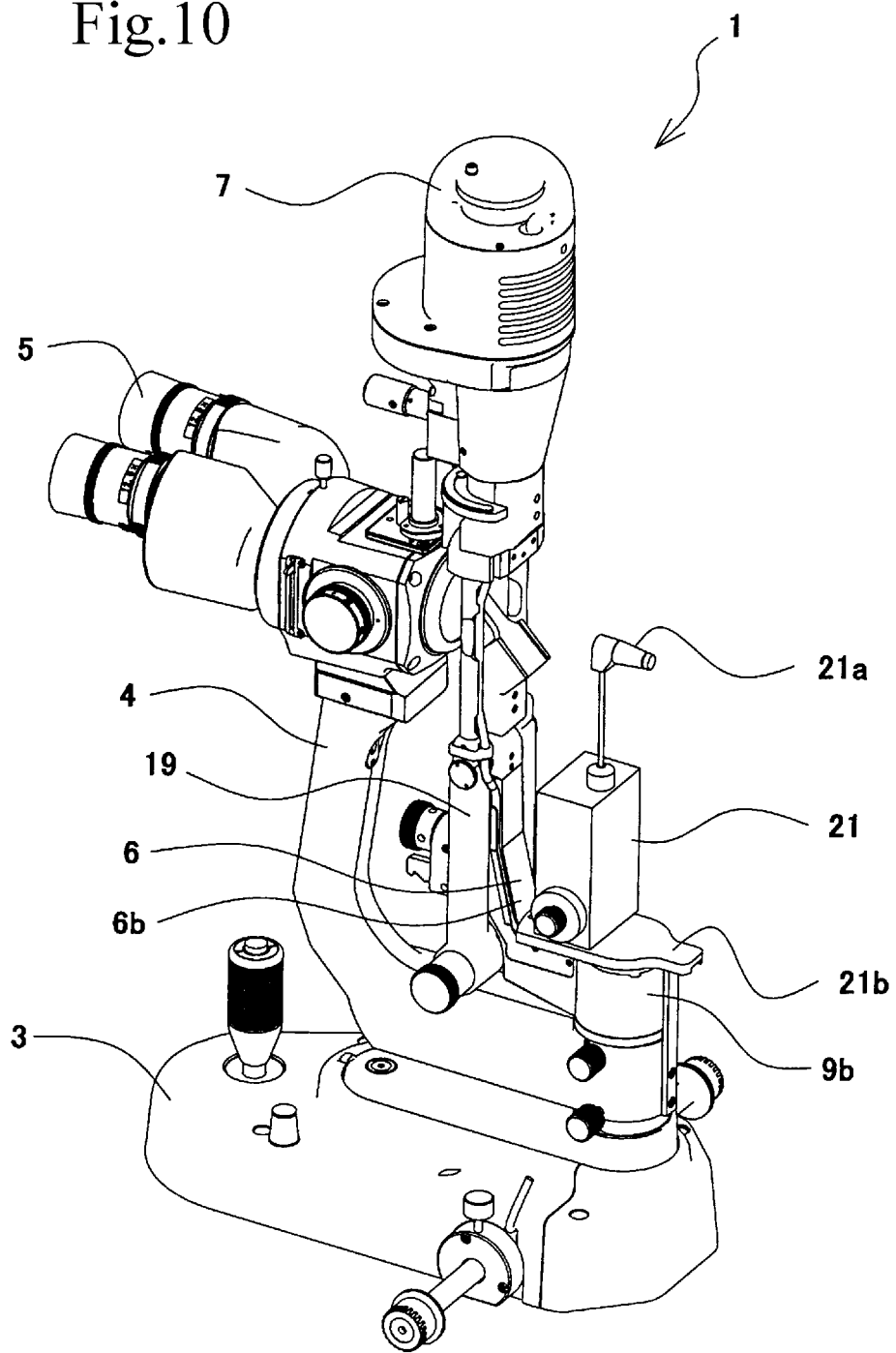
FIG. 10 is a perspective view, including views of the right side surface, the back surface, and the top surface, showing a state in which a standing-type tonometer is attached to the slit lamp microscope in FIG. 1.

As shown in FIG. 10, a standing-type tonometer 21 may be attached to the top of the tubular accommodating part 9b, which accommodates the swivel shaft 11 of the slit lamp microscope 1 according to this embodiment. When the standing-type tonometer 21 is attached, a prism 21a of the tonometer 21 needs to be located on the axis of the swivel shaft 11. However, because the dimensions of the tonometer 21 vary among manufacturers, an attachment adapter 21b suitable for each tonometer 21 need to be attached. Hence, when the standing-type tonometer 21 is attached, it is necessary to ensure a sufficient space between the swivel shaft 11 and the arm body 6b.

From this standpoint, when, for example, the illumination-unit-side cable 13b is disposed in the inner space of the illumination support arm 6, because the microscope support arm 4 and the illumination support arm 6 are rotatable, it is necessary to increasing the inner space of the swivel shaft 11 and to dispose the illumination-power-supply cable 13 in a slack manner. This makes it difficult to ensure a sufficient space between the arm body 6b and the tubular accommodating part 9b, which accommodates the swivel shaft 11. In contrast, in this embodiment, because the cable holder 6f, in which the illumination-unit-side cable 13b is disposed, is provided, and the illumination-unit-side cable 13b is not disposed in the inner space of the illumination support arm 6, it is possible to ensure a sufficient space between the arm body 6b and the tubular accommodating part 9b accommodating the swivel shaft 11. Hence, it is possible to install the adapter 21b and the standing-type tonometer 21 on the tubular accommodating part 9b.

[Modifications]

The above-described embodiment can be implemented in the form of modifications, and examples thereof will be described below.

Figure 11A:
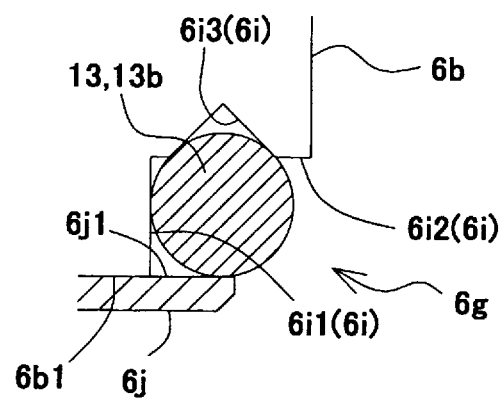
FIG. 11 includes sectional views corresponding to FIG. 6, showing modifications of the first groove-shaped holder.
Figure 11B:
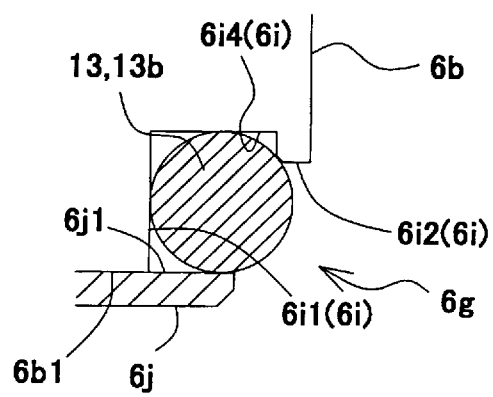

In the embodiment above, although the first groove-shaped holder 6g including the step portion 6i and the holding plate 6j has been shown, for example, a modification shown in FIG. 11 is also possible. In the modification in FIG. 11(a), a V groove 6i3, serving as a "locking part" in which the illumination-power-supply cable 13 (illumination-unit-side cable 13b) is fitted is formed in the groove side surface 6i2 of the arm body 6b. Similarly, FIG. 11(b) shows a configuration in which a recess 6i4, serving as a "locking part", is formed. In these modifications, the holding plate 6j is not provided with the holding part 6j2. Also in these modifications, it is possible to reliably hold the illumination-power-supply cable 13 in the first groove-shaped holder 6g.

Figure 12A:
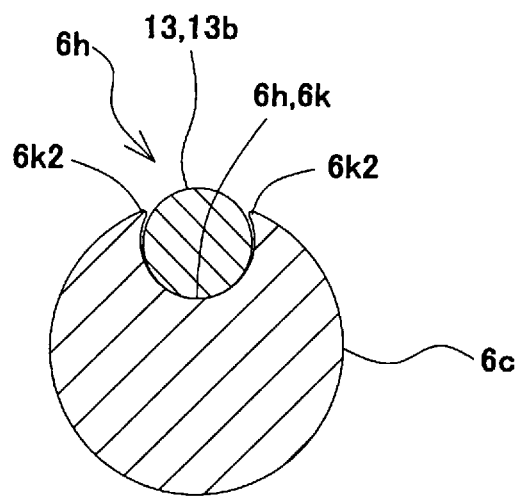
FIG. 12 includes sectional views corresponding to FIG. 4(c), showing modifications of the second groove-shaped holder.
Figure 12B:
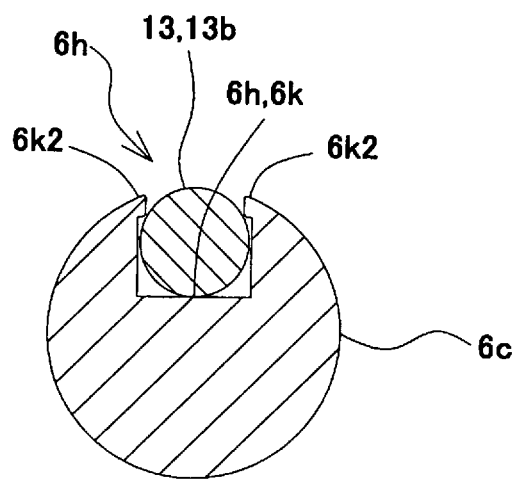

In the embodiment above, although the second groove-shaped holder 6h with the holding groove 6k having a trapezoidal sectional shape has been shown as an example, the holding groove 6k may have sectional shapes as shown in modifications in FIG. 12. FIG. 12(a) shows a holding groove 6k having a circular sectional shape, and FIG. 12(b) shows a holding groove 6k having a square-groove-shaped sectional shape. Both holding grooves 6k are provided with holding parts 6k2 for preventing the illumination-power-supply cable 13 (illumination-unit-side cable 13b) from coming off. In these modifications, it is possible to reliably hold the illumination-power-supply cable 13 in the second groove-shaped holder 6h.

In the embodiment above, although the background-illumination unit 16 having the optical system 16b has been described as an example, the optical system 16b may be omitted, depending on the directivity of the light emitted from the background-illumination light source 16a.

A camera unit (not shown) may be attached to the microscope unit 5 according to the embodiment above.

REFERENCE SIGNS LIST 1 slit lamp microscope
2 mounting frame
3 sliding base (support base)
4 microscope support arm
4a cable protection tube
4b first extending part
4c bent portion
4d second extending part
4e fitting part
4f1 cover
4f2 cover
5 microscope unit
6 illumination support arm
6a cable protection tube
6b arm body
6b1 side surface
6b2 connecting hollow part
6b3 communication port
6b4 cover
6c shaft
6d shaft
6e fitting part
6f cable holder
6g first groove-shaped holder
6h second groove-shaped holder
6i step portion
6i1 groove bottom surface
6i2 groove side surface
6i3 V groove (locking part)
6i4 recess (locking part)
6j holding plate 6j1 groove side surface
6j2 holding part (locking part)
6j3 slit
6k holding groove
6k1 guide slope
6k2 holding part (locking part)
7 illumination unit
7a housing
7b light source
7c illumination optical system
7d cable insertion groove
8 chin rest unit
9 base body
9a housing
9b tubular accommodating part
10 driving unit
11 swivel shaft
11a lower attachment part
11b upper attachment part
11c movement-allowing hole
11c1 hole edge (pivot restricting portion)
11d cable insertion hole
12 substrate
13 illumination-power-supply cable
13a substrate-side cable
13a1 connector
13b illumination-unit-side cable
13b1 connector
14 background-illumination-power-supply cable
14a substrate-side cable
14a1 connector
14b background-illumination-unit-side cable
14b1 connector
15 joystick
16 background-illumination unit
16a background-illumination light source
16b optical system
17 reflection mirror
18 pivot shaft
19 support frame
19a deformation allowance groove
19b cable holder
20 light-source-diverting-type background illumination device
21 standing-type tonometer
21a prism
21b adapter

The invention claimed is:

1. A slit lamp microscope comprising:
an illumination unit that illuminates an eye to be examined;
an illumination support arm to which the illumination unit is attached;
a support base to which the illumination support arm is attached; and
an illumination-power-supply cable disposed along the illumination support arm from a support base side to the illumination unit,
wherein the illumination support arm has a groove-shaped cable holder in which the illumination-power-supply cable is disposed along an outer surface of the illumination support arm, the groove-shaped cable holder has a groove formed on and along the illumination support arm, the groove is exposed outside without a cover configured to hold the illumination-power-supply cable in an externally exposed state.

2. The slit lamp microscope according to claim 1, wherein the cable holder has a locking part that prevents the illumination-power-supply cable disposed therein from coming off.

3. The slit lamp microscope according to claim 1, further comprising:
a microscope unit that is used to observe the eye to be examined; and
a microscope support arm that is attached to the microscope unit at a distal end thereof and is attached to the support base at a base end thereof,
wherein the microscope support arm has a background-illumination light source that illuminates the eye to be examined.

4. The slit lamp microscope according to claim 3, wherein the background-illumination light source is disposed at a position facing the illumination support arm.

5. The slit lamp microscope according to claim 3, further comprising a background-illumination-power-supply cable, wherein
the microscope support arm has a hollow tubular inner space, and
the background-illumination-power-supply cable is disposed through the inner space of the microscope support arm from the support base side to the background-illumination light source.

6. The slit lamp microscope according to claim 1, further comprising a swivel shaft that allows the illumination support arm to pivot in a horizontal direction, relative to the support base,
wherein the swivel shaft has a pivot restricting portion that restricts a pivot area of the illumination support arm.

7. The slit lamp microscope according to claim 6, further comprising a standing-type tonometer above the swivel shaft of the support base.

8. A slit lamp microscope comprising:
an illumination unit that illuminates an eye to be examined;
an illumination support arm to which the illumination unit is attached;
a support base to which the illumination support arm is attached; and
an illumination-power-supply cable disposed along the illumination support arm from a support base side to the illumination unit,
wherein the illumination support arm has a groove-shaped cable holder in which the illumination-power-supply cable is disposed along an outer surface of the illumination support arm in an externally exposed state,
wherein the illumination support arm has an arm body attached to the support base, and at least one columnar shaft extending from the arm body to the illumination unit, and
the cable holder has a first groove-shaped holder provided in the arm body and a second groove-shaped holder provided in the shaft.

9. The slit lamp microscope according to claim 8, wherein the first groove-shaped holder has a step portion that is formed in an outer surface of the arm body and constitutes a groove bottom surface and a groove side surface of the first groove-shaped holder, and a holding plate that constitutes a groove side surface facing the groove side surface of the step portion.

10. The slit lamp microscope according to claim 8, wherein the second groove-shaped holder has a holding groove extending in a longitudinal direction of the shaft, the holding groove having a guide slope that gently bends and guides the illumination-power-supply cable.

11. The slit lamp microscope according to claim 8, wherein a deformation allowance groove that allows flexural deformation of the illumination-power-supply cable is provided between the arm body and the shaft.

* * * * *